United States Patent
Fleitz et al.

(10) Patent No.: US 9,441,254 B2
(45) Date of Patent: Sep. 13, 2016

(54) PROCESS FOR THE PREPARATION OF AN INTERMEDIATE FOR AN OREXIN RECEPTOR ANTAGONIST

(71) Applicant: Merck Sharp & Dohme Corp., Rahway, NJ (US)

(72) Inventors: Fred Fleitz, Germantown, WI (US); Ian Mangion, Cranford, NJ (US); Jingjun Yin, Green Brook, NJ (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 14/399,138

(22) PCT Filed: May 6, 2013

(86) PCT No.: PCT/US2013/039610
§ 371 (c)(1),
(2) Date: Nov. 5, 2014

(87) PCT Pub. No.: WO2013/169610
PCT Pub. Date: Nov. 14, 2013

(65) Prior Publication Data
US 2015/0284753 A1    Oct. 8, 2015

Related U.S. Application Data

(60) Provisional application No. 61/644,559, filed on May 9, 2012.

(51) Int. Cl.
| | |
|---|---|
| *C12P 17/16* | (2006.01) |
| *C12P 17/18* | (2006.01) |
| *C12N 9/10* | (2006.01) |
| *A61K 31/4985* | (2006.01) |

(52) U.S. Cl.
CPC ............ *C12P 17/16* (2013.01); *A61K 31/4985* (2013.01); *C12N 9/1096* (2013.01); *C12P 17/182* (2013.01); *C12Y 401/01028* (2013.01)

(58) Field of Classification Search
CPC ..... C12N 9/00; C12N 9/1096; C12P 17/182; C12Y 401/01028
USPC .................................................. 435/118, 15
See application file for complete search history.

(56) References Cited

U.S. PATENT DOCUMENTS

| 7,951,797 B2 | 5/2011 | Breslin et al. |
| 8,674,093 B2 | 3/2014 | Campeau et al. |
| 2013/0331379 A1 | 12/2013 | Baxter |

FOREIGN PATENT DOCUMENTS

| WO | WO2007126935 | 11/2007 |
| WO | WO2008069997 | 6/2008 |
| WO | WO2012148553 | 11/2012 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
C. Baxter et al., The First Large-Scale synthesis of MK-4305: A Dual Orexin Receptor Antagonist for the Treatment of Sleep Disorder, Organic Process and Research & Development, 2011, pp. 367-375, vol. 15(2).
Cox, et al., "Discovery of the Dual Orexin Receptor Antagonist [(7R)-4-(5-Chloro-1,3-benzoxazol-2-yl)-7-methyl-1,4diazepan . . . ", J. Med. Chem, 2010, p. 5320-5332, vol. 53.
N. Strotman et al., Reaction Development and Mechanistic Study of a Ruthenium Catalyzed Intramolecular Asymmetric Reductive Amination en Route to the Dual Orexin Inhibitor Suvorexant (MK-4305), JACS, 2011, pp. 8362-8371, vol. 133(21).
Extended European Search Report and Opinion for EP2847343 (Mar. 8, 2016).
Girardin, Convergent Kilogram-Scale Synthesis of Dual Orexin Receptor Antagonist, Organic Process Research & Development, 2012, 61-68, 17.
I. Mangion et al, Enantioselective Synthesis of a Dual Orexin Receptor Antagonist, Org. Letters, 2012, 3458-3461, 14(13).
Kroutil, Asymmetric Preparation of PRIM-, SEC-, and TERT-Amines Employing Selected Biocatalysts, Organic Process Research & Development, 2013, 751-759, 17.
Radi, Suvorexant, Drugs of the Future, 2013, 27-36, 38(1).

* cited by examiner

*Primary Examiner* — Md. Younus Meah
(74) *Attorney, Agent, or Firm* — J. Eric Thies; John C. Todaro

(57) ABSTRACT

The present invention is directed to processes for preparing an intermediate for a diazepane compound which is an antagonist of orexin receptors, and which is useful in the treatment or prevention of neurological and psychiatric disorders and diseases in which orexin receptors are involved.

11 Claims, No Drawings

SEQUENCE LISTING

```
<160> NUMBER OF SEQ ID NOS: 1

<210> SEQ ID NO 1
<211> LENGTH: 330
<212> TYPE: PRT
<213> ORGANISM: Artificial Sequence
<220> FEATURE:
<223> OTHER INFORMATION: Synthetic Sequence

<400> SEQUENCE: 1

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Thr Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
```

| | | | | |
|---|---|---|---|---|
| 305 | 310 | 315 | 320 | |
| Pro Ser Ser Leu Leu Thr Pro Val Gln Tyr | | | | |
| | 325 | | 330 | |

PROCESS FOR THE PREPARATION OF AN INTERMEDIATE FOR AN OREXIN RECEPTOR ANTAGONIST

BACKGROUND OF THE INVENTION

The orexins (hypocretins) comprise two neuropeptides produced in the hypothalamus: the orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behavior (Sakurai T. et al., Cell, 1998, 92, 573-585). Orexins regulate states of sleep and wakefulness opening potentially novel therapeutic approaches for narcoleptic or insomniac patients (Chemelli R. M. et al., Cell, 1999, 98, 437-451). Orexins have also been indicated as playing a role in arousal, reward, learning and memory (Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A and the orexin-2 receptor (OX2 or OX2R) is capable to bind OX-A as well as OX-B. The physiological actions in which orexins are presumed to participate are thought to be expressed via one or both of OX1 receptor and OX2 receptor as the two subtypes of orexin receptors.

Orexin receptors are found in the mammalian brain and the scientific literature suggests that they may be involved in various pathologies such as depression; anxiety; addictions; obsessive compulsive disorder; affective neurosis; depressive neurosis; anxiety neurosis; dysthymic disorder; behaviour disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders such as anorexia, bulimia, cachexia, and obesity; addictive feeding behaviors; binge/purge feeding behaviors; cardiovascular diseases; diabetes; appetite/taste disorders; emesis, vomiting, nausea; asthma; cancer; Parkinson's disease; Cushing's syndrome/disease; basophile adenoma; prolactinoma; hyperprolactinemia; hypophysis tumour/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; conditions associated with visceral pain such as irritable bowel syndrome, and angina; migraine; urinary bladder incontinence e.g. urge incontinence; tolerance to narcotics or withdrawal from narcotics; sleep disorders; sleep apnea; narcolepsy; insomnia; parasomnia; jet lag syndrome; and neurodegenerative disorders including nosological entities such as disinhibition-dementia-parkinsonism-amyotrophy complex; pallido-ponto-nigral degeneration; epilepsy; seizure disorders and other diseases related to general orexin system dysfunction.

The compound of the formula I:

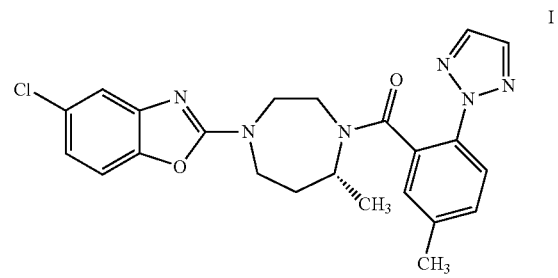 [SMILES: Cc1ccc(-n2nccn2)c(C(=O)N2CCN(c3nc4cc(Cl)ccc4o3)CC[C@H]2C)c1]

5-chloro-2-{(5R)-5-methyl-4-[5-methyl-2-(2H-1,2,3-triazol-2-yl)benzoyl]-1,4-diazepan-1-yl}-1,3-benzoxazole (suvorexant) is disclosed as an antagonist of orexin receptors in U.S. Pat. No. 7,951,797, US Patent Application Publication US 2008/0132490, PCT Patent Publication WO 2008/069997, Cox et al., J. Med. Chem. 2010, 53, 5320-5332, Strotman et al., JACS, 2011, 133(21), 8362-8371, Baxter et al., Org. Process Res. & Dev., 2011, 15(2) 367-375. This compound may be named as, e.g., "5-chloro-2-{(5R)-5-methyl-4-[5-methyl-2-(2H-1,2,3-triazol-2-yl)benzoyl]-1,4-diazepan-1-yl}-1,3-benzoxazole," "[(R)-4-(5-chloro-benzoxazol-2-yl)-7-methyl-[1,4]diazepan-1-yl]-(5-methyl-2-[1,2,3]triazol-2-yl-phenyl)-methanone" or "[(7R)-4-(5-chloro-1,3-benzoxazol-2-yl)-7-methyl-1,4-diazepan-1-yl][5-methyl-2-(2H-1,2,3-triazol-2-yl)phenyl]methanone."

SUMMARY OF THE INVENTION

The present invention is directed to processes for preparing an intermediate for a diazepane compound which is an antagonist of orexin receptors, and which is useful in the treatment or prevention of neurological and psychiatric disorders and diseases in which orexin receptors are involved.

DETAILED DESCRIPTION OF THE INVENTION

The present invention is directed to a process for preparing a compound of the formula III:

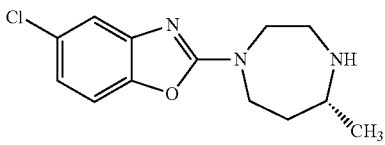

or a salt thereof,
which comprises:
contacting a compound of the formula IV:

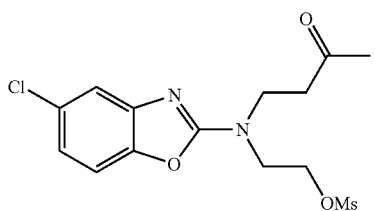

with a transaminase polypeptide in the presence of a cofactor and in the presence of a weak base, to give the compound of the formula III, or a salt thereof.

In an embodiment of the present invention, the transaminase polypeptide is selected from a transaminase polypeptide having the amino acid sequence disclosed in US Patent Publication US 2010/0285541 as "SEQ ID NO:109" to "SEQ ID NO:168" therein. In an embodiment of the present invention, the transaminase polypeptide is selected from a transaminase polypeptide having the amino acid sequence disclosed in US Patent Publication US 2010/0285541 as "SEQ ID NO:67" to "SEQ ID NO:108" therein. In an embodiment of the present invention, the transaminase polypeptide is selected from a transaminase polypeptide having the amino acid sequence disclosed in US Patent Publication US 2010/0285541 as "SEQ ID NO:110" therein. In an embodiment of the present invention, the transaminase polypeptide is selected from a transaminase polypeptide having the amino acid sequence disclosed in US Patent Publication US 2010/0285541 as "SEQ ID NO:104" therein. Methods for making transaminase polypeptides and using them for biocatalytic synthesis are well-known in the art, such as in US Patent Publication US 2010/0285541, hereby incorporated by reference.

In an embodiment of the present invention, the transaminase polypeptide is a transaminase polypeptide having the amino acid sequence SEQ ID NO:1:

```
Met Ala Phe Ser Ala Asp Thr Pro Glu Ile Val Tyr
1               5                   10

Thr His Asp Thr Gly Leu Asp Tyr Ile Thr Tyr Ser
        15                  20

Asp Tyr Glu Leu Asp Pro Ala Asn Pro Leu Ala Gly
25                  30                  35

Gly Ala Ala Trp Ile Glu Gly Ala Phe Val Pro Pro
            40                  45

Ser Glu Ala Arg Ile Ser Ile Phe Asp Gln Gly Phe
    50                  55                  60

Tyr Thr Ser Asp Ala Thr Tyr Thr Thr Phe His Val
                65                  70

Trp Asn Gly Asn Ala Phe Arg Leu Gly Asp His Ile
        75                  80

Glu Arg Leu Phe Ser Asn Ala Glu Ser Ile Arg Leu
85                  90                  95

Ile Pro Pro Leu Thr Gln Asp Glu Val Lys Glu Ile
                100                 105

Ala Leu Glu Leu Val Ala Lys Thr Glu Leu Arg Glu
        110                 115                 120

Ala Met Val Thr Val Thr Ile Thr Arg Gly Tyr Ser
                125                 130

Ser Thr Pro Phe Glu Arg Asp Ile Thr Lys His Arg
        135                 140

Pro Gln Val Tyr Met Ser Ala Cys Pro Tyr Gln Trp
145                 150                 155

Ile Val Pro Phe Asp Arg Ile Arg Asp Gly Val His
                160                 165

Leu Met Val Ala Gln Ser Val Arg Arg Thr Pro Arg
    170                 175                 180

Ser Ser Ile Asp Pro Gln Val Lys Asn Phe Gln Trp
                185                 190

Gly Asp Leu Ile Arg Ala Ile Gln Glu Thr His Asp
        195                 200

Arg Gly Phe Glu Leu Pro Leu Leu Leu Asp Cys Asp
205                 210                 215

Asn Leu Leu Ala Glu Gly Pro Gly Phe Asn Val Val
                220                 225

Val Ile Lys Asp Gly Val Val Arg Ser Pro Gly Arg
    230                 235                 240

Ala Ala Leu Pro Gly Ile Thr Arg Lys Thr Val Leu
                245                 250

Glu Ile Ala Glu Ser Leu Gly His Glu Ala Ile Leu
        255                 260

Ala Asp Ile Thr Pro Ala Glu Leu Tyr Asp Ala Asp
265                 270                 275

Glu Val Leu Gly Cys Ser Thr Gly Gly Gly Val Trp
                280                 285

Pro Phe Val Ser Val Asp Gly Asn Ser Ile Ser Asp
        290                 295                 300

Gly Val Pro Gly Pro Val Thr Gln Ser Ile Ile Arg
                305                 310

Arg Tyr Trp Glu Leu Asn Val Glu Pro Ser Ser Leu
        315                 320

Leu Thr Pro Val Gln Tyr
325                 330
```

In an embodiment of the present invention, the transaminase polypeptide is ATA-117. The transaminase polypeptide ATA-117 is commercially available from Codexis, Inc. (Redwood City, Calif., USA).

In an embodiment of the present invention, the cofactor is a member of the vitamin B6 family. In an embodiment of the present invention, the cofactor is selected from the group consisting of pyridoxal (PL), pyridoxamine (PM), pyridoxine phosphate (PNP), pyridoxamine phosphate (PMP), and pyridoxal 5'-phosphate. In an embodiment of the present invention, the cofactor is pyridoxal 5'-phosphate. In an embodiment of the present invention, the weak base is selected from triethylamine, Hunig's base, triethanolamine, DBU, an inorganic carbonate, an inorganic bicarbonate, an inorganic phosphate, and an inorganic hydroxide. In an embodiment of the present invention, the solvent for the process comprises a solvent that is selected from NMP (1-methyl-2-pyrroldinone), NEP (1-ethyl-2-pyrroldinone), DMSO, DMF, MeOH, acetonitrile and water. In an embodiment of the present invention, the process is conducted at a temperature between about 20 and 60° C.

In an alternate embodiment, the present invention is directed to a product prepared by any of the processes disclosed herein.

The compound of the formula III may be employed to prepare the compound of the formula I:

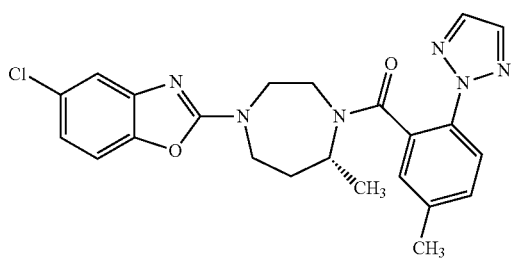

I or a pharmaceutically acceptable salt thereof,
by contacting a compound of the formula II:

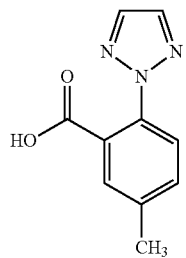

II with an activating agent to form the acid chloride,
followed by contacting the acid chloride with a compound of the formula III:

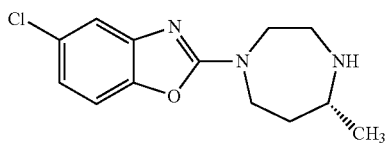

III or a salt thereof,
in the presence of a weak base to give the compound of the formula I, or a pharmaceutically acceptable salt thereof.

The compound of the formula I is disclosed as an antagonist of orexin receptors in U.S. Pat. No. 7,951,797, US Patent Application Publication US 2008/0132490, PCT Patent Publication WO 2008/069997, Cox et al., J. Med. Chem. 2010, 53, 5320-5332, Strotman et al., JACS, 2011, 133(21), 8362-8371, and Baxter et al., Org. Process Res. & Dev., 2011, 15(2) 367-375. This compound is disclosed as having activity in antagonizing the human orexin-1 (OX1) receptor with a Ki of 0.55 nM and in antagonizing the human orexin-2 (OX2) receptor with a Ki of 0.35 nM. The processes disclosed in U.S. Pat. No. 7,951,797, US Patent Application Publication US 2008/0132490, PCT Patent Publication WO 2008/069997, Cox et al., J. Med. Chem. 2010, 53, 5320-5332, Strotman et al., JACS, 2011, 133(21), 8362-8371, and Baxter et al., Org. Process Res. & Dev., 2011, 15(2) 367-375 are lengthy, suffer from low yields, necessitate multiple protecting groups, rely on chiral chromatography to prepare a single isomer and require microwave technology to prepare the acid intermediate. Relative to the processes disclosed in U.S. Pat. No. 7,951,797, US Patent Application Publication US 2008/0132490, PCT Patent Publication WO 2008/069997, Cox et al., J. Med. Chem. 2010, 53, 5320-5332, Strotman et al., JACS, 2011, 133(21), 8362-8371, and Baxter et al., Org. Process Res. & Dev., 2011, 15(2) 367-375, the present invention may provide improved processes for the efficient, scalable, chromatography-free and cost-effective preparation of the formula I, to give higher isolated yield of the subject compound. The processes of the present invention may increase the efficiency of the synthetic route to the desired product by reducing the number steps and allowing access to a single enantiomer without recourse to chromatography. In addition, the use of protecting groups is minimized, low yielding steps are reduced, and an enzymatic transformation is employed to establish the chiral center. In accordance with the present invention, the use of an enzymatic transformation may also provide higher enantioselectivity than metal catalysis and avoids the use of toxic transition metals. Such processes may also provide a lower cost with respect to certain reagents and starting materials. In accordance with the present invention, the use of an enzymatic transformation may also reduce the use of potentially carcinogenic solvents such as dichloromethane.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the Formulas of the invention, it is understood that both the (R) and (S) configurations of the chiral carbon, and hence both enantiomers and mixtures thereof, are embraced within the Formula. For example, Formula I shows the structure of the compound with the designation of specific stereochemistry. When the compounds of the present invention contain one chiral center, the term "stereoisomer" includes both enantiomers and mixtures of enantiomers, such as the specific 50:50 mixture referred to as a racemic mixtures.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$ alkyl is defined to identify the group as having 1, 2, 3, 4, 5 or 6 carbons in a linear or branched arrangement, such that $C_{1-6}$ alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to final compounds of Formula I are meant to also include the pharmaceutically acceptable salts.

The term "salts" refers to salts prepared from acceptable bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from organic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids.

Exemplifying the invention is the use of the compounds disclosed in the Examples and herein. Specific compounds within the present invention include a compound which selected from the group consisting of the compounds disclosed in the following Examples and salts thereof and individual enantiomers or diastereomers thereof.

Several methods for preparing the subject compounds are illustrated in the following Schemes and Examples. Starting materials are made according to procedures known in the art or as illustrated herein. The following abbreviations are used herein: 2-MeTHF: 2-methyltetrahydrofuran; Ac: acetyl; Ar: aryl; AY: assay yield; Bn: benzyl; Boc: tert-butyloxy carbonyl; $Boc_2O$: di-tert-butyldicarbonate; BSA: bovine serum albumin; Cbz: carbobenzyloxy; CDI: carbonyl diimidazole; CSA: camphor sulfonic acid; DEAD: diethylazodicarboxylate; DCE: dichloroethane; DCM: dichloromethane; DIPEA: N,N-diisopropylethylamine; DMF: N,N-dimethylformamide; DMSO: dimethylsulfoxide; EDC: N-(3-dimethylaminopropyl)-N'-ethylcarbodiimide; Et: ethyl; EtOH: ethanol; $Et_3N$: triethylamine; HOBT: hydroxybenzotriazole hydrate; Me: methyl; MTBE: methyl tert-butyl ether; NAD: nicotinamide adenine dinucleotide; NMP: N-methylpyrrolidone; Ph: phenyl; PhMe: toluene; PLP: pyridoxal-5' phosphate; rt: room temperature; $SOCl_2$: thionyl chloride; $T_3P$: 1-propylphosphonic anhydride; t-Bu: tert-butyl; TsCl: tosyl chloride; TFA: trifluoracetic acid; THF: tetrahydrofuran. The processes of the present invention can be conducted in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes and examples may be varied to facilitate the

EXAMPLE 1

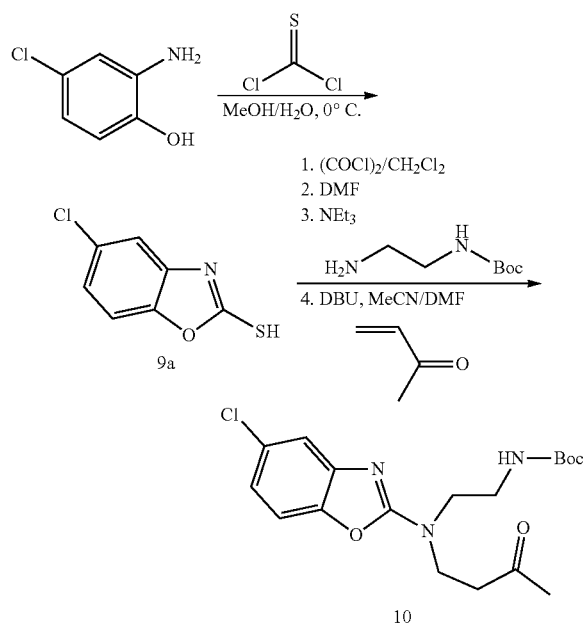

5-Chloro-1,3-benzoxazole-2-thiol (9a)

2-Amino-4-chlorophenol (2.50 kg, 17.4 mol) was charged to a vessel and suspended in water (52 L) and methanol (10.4 L). High dilution was required to prevent slow and difficult filtration of the product. The mixture was stirred, cooled to 0° C., then thiophosgene (2.00 kg, 17.4 mol) was added to the suspension ensuring that the internal temperature remained at 5° C. throughout the addition. Water (8 L) and methanol (2 L) were added to aid stirring and the slurry warmed to 13° C. for 1 h, followed by aging at 20° C. for a further 1 h. The slurry was then filtered and the solid washed with water (5 L). The batch was repeated and combined to dry in a vacuum oven (T=40° C.) for 15 h to give 9-a (5.81 kg, 31.3 mol). The data corresponds to the commercially available material. $^1$H NMR (400 MHz, $d_6$-DMSO): δ 7.51 (d, 1H, J=9.2 Hz), 7.307.26 (m, 2H). $^{13}$C NMR (100.6 MHz, $d_6$-DMSO): δ 181.2, 147.4, 133.1, 129.7, 123.9, 111.6, 110.8. HRMS (ESI): m/z [M$^+$+H] calcd for $C_7H_4ClNOS$: 185.9780; found: 185.9785.

{2-[(5-Chloro-benzooxazol-2-yl)-(3-oxo-butyl)-amino]-ethyl}-carbamic acid tert-butyl ester (10)

Thiol 9a (10.5 kg, 54.6 mol) was added to a vessel and suspended in DCM (141 kg). Oxalyl chloride (10.4 kg, 82.3 mol) was added (slightly endothermic) followed by DMF (40.0 kg, 547 mol) over 1.25 h, such that the batch temperature was ≤25° C. The batch was aged at 20° C. for approximately 30 min, HPLC analysis showed reaction to be complete. The batch was cooled to 10° C. then triethylamine (16.64 kg, 164.4 mol) was added via a sub-surface sample line at such a rate as to maintain a batch temperature of ≤10° C. A sub-surface addition protocol was required to prevent build up of triethylamine hydrochloride solid on the walls of the vessel. The batch was cooled to 0° C., then a solution of N-Boc-ethylenediamine (10.5 kg, 61.2 mol) in DCM (10 kg) was added such that the batch temperature was ≤10° C. The reaction was warmed to 20° C. and stirred for 2.5 h, HPLC analysis showed the reaction to be complete. Water (63.6 kg) was charged to the batch and the mixture stirred for 5 min. The layers were separated and the aqueous phase re-extracted with DCM (42.2 kg). The organic solutions were then combined and approximately half of the total DCM volume was distilled from the batch under vacuum whilst maintaining a temperature of ≤40° C. MeCN (83.3 kg) was then added and the remaining DCM removed by distillation (0.5 mol % DCM left by $^1$H NMR wrt MeCN). MVK (4.61 kg, 65.8 mol) was added to the batch followed by DBU (4.17 kg, 27.4 mol) such that the temperature was ≤20° C. The batch was aged for 10 h at 20° C. then analyzed by HPLC. The reaction was then diluted with water (42.4 kg) and aged for a further 30 min. The mixture was filtered and the slurry washed with MeCN (33.3 kg). The solid was washed with MeCN (~10 L) then dried in a vacuum oven (T=60° C.) for 22 h. MVK adduct 10 (15.5 kg) was isolated as an off-white solid. mp 145-148° C. $^1$H NMR (400 MHz, CDCl$_3$): δ 7.24 (d, 1H, J=2.3 Hz), 7.09 (d, 1H, J=8.5 Hz), 6.91 (dd, 1H, J=8.5, 2.3 Hz), 5.06 (s, 1H, br), 3.73 (t, 2H, J=6.7 Hz), 3.63 (t, 2H, J=6.1 Hz), 3.37 (d, 2H, br), 2.89 (t, 2H, J=6.7 Hz), 2.14 (s, 3H), 1.33 (s, 9H). $^{13}$C NMR (100.6 MHz, CDCl$_3$): δ 206.7, 163.0, 156.0, 147.4, 144.6, 129.2, 120.3, 116.6, 109.2, 79.4, 49.3, 44.3, 41.9, 39.1, 30.2, 28.3. HRMS (ESI): m/z [M$^+$+H] calcd for $C_{18}H_{24}ClN_3O_4$: 382.1534; found: 382.1544.

EXAMPLE 2

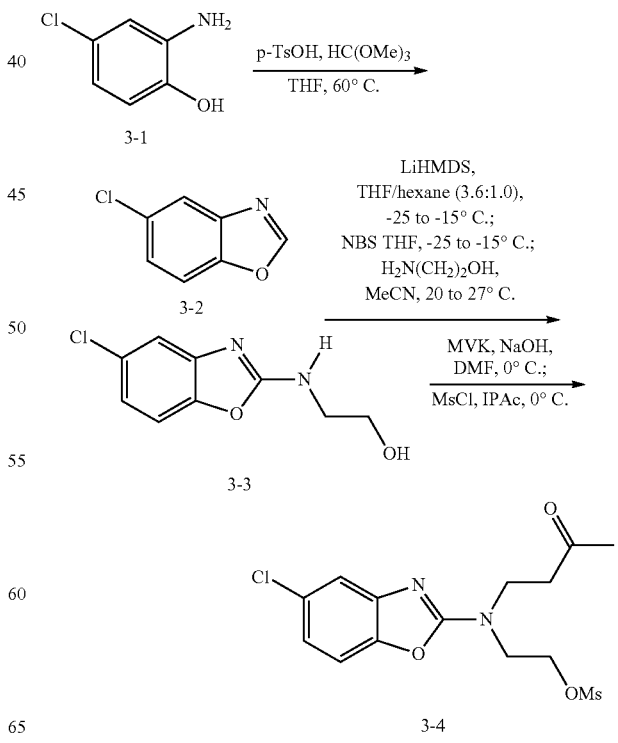

5-Chlorobenzoxazole (3-2)

To a 250 mL 3-neck round bottom flask equipped with a distillation head, glass stopper, septum, thermocouple and magnetic stir bar was charged 2-amino-4-chlorophenol (20.00 g, 0.139 mol). The solid was dissolved in THF (60 mL) and p-TsOH (0.265 g, 1.39 mmol) was added. The brown solution was warmed to 60° C. over 10 min and aged for 90 min. HPLC assay of the reaction mixture showed 1 LCAP unreacted starting material. The temperature was increased from 60° C. to 74° C., and at 63° C. solvent distillation began. A total of 58 mL was collected during the first distillation. The mixture was diluted with THF (60 mL) and a total of 67 mL of solvent was removed between 71 and 84° C. The mixture was again diluted with THF (60 mL) and 61 mL of solvent was removed between 74 and 114° C. The dark brown solution was cooled to room temperature. The final mass of the solution was 27.96 g. Analysis of the crude stream by $^1$H NMR showed 0.1 wt % MeOH present in the sample. $^1$H NMR (500 MHz, CDCl$_3$): δ=8.10 (s, 1H), 7.76 (d, J=1.5 Hz, 1H), 7.50 (d, J=8.7 Hz, 1H), 7.36 ppm (dd, J=8.7, 1.7 Hz, 1H).

2-[(5-Chloro-1,3-benzoxazol-2-yl)amino]ethanol (3-3)

A 500 mL 3-neck round bottom flask equipped with a septum, thermocouple, 125 mL addition funnel, inert gas inlet and magnetic stir bar was purged with nitrogen for 10 min. Hexamethyldisilazane (42 mL, 0.20 mol) and THF (78 mL) were charged against positive nitrogen pressure. The addition funnel was charged with a hexane solution of n-butyllithium (78.0 mL, 195 mmol). The amine solution was cooled to −52° C. and n-butyllithium was added over 84 min, resulting in a temperature increase to 12.5° C. over the course of the addition. The resulting lithium hexamethyldisilazide solution was removed from the cooling bath and aged for 30 minutes. To a 500 mL 3-neck round bottom flask equipped with a septum, thermocouple, inert gas inlet and magnetic stir bar was charged 5-chlorobenzoxazole (20.00 g, 130 mmol). The gray solid was dissolved in THF (100 mL) and the resulting colorless solution was cooled to −25° C. The freshly prepared lithium hexamethyldisilazide solution was added via cannula over 80 minutes. The temperature of the anion solution was maintained between −25 and −15° C. during the addition. The resulting dark brown solution was aged for 90 minutes between −25 and −15° C. To a 1000 mL 3-neck round bottom flask equipped with a Claisen adapter, septum, thermocouple, inert gas inlet, stir rod bearing, and blade was charged THF (100 mL) and N-bromosuccinimide (34.8 g, 195 mmol). The resulting slurry was cooled to −20° C. and the anion solution was added via cannula over 150 minutes. During the addition the anion solution and reaction mixture were maintained between −25 and −15° C. The resulting brown slurry was removed from the cooling bath and aged for 50 minutes while warming to room temperature. To the resulting bromide slurry was added a solution of ethanolamine (12.6 mL, 208 mmol) in MeCN (38 mL) via syringe pump over 5 hours. During the addition the reaction temperature was maintained between 20 and 27° C. The resulting brown slurry was aged at room temperature overnight. The reaction mixture was cooled in an ice water bath and the septum replaced with a 50 mL addition funnel charged with concentrated HCl (32 mL, 390 mmol). The acid solution was added over 10 min, during which time the addition temperature increased from 10 to 20° C. The reaction mixture was removed from the ice water bath and aged for 5 min. A 20% (w/w) solution of K$_2$HPO$_4$ in water (170 mL) was added and the resulting biphasic mixture was transferred to a seperatory funnel. The flask was washed with THF (3×, 10 mL) and the washings were added. The aqueous phase was cut; the organic phase was washed with 20% (w/w) K$_2$HPO$_4$ in water (200 mL), separated and analyzed. The crude reaction stream had a total mass of 396.47 g. By quantitative HPLC assayed 25.81 g of 3-3 in the organic phase. $^1$H NMR (500 MHz, DMSO-d$_6$): δ=8.17 (t, J=5.6 Hz, 1H), 7.34 (d, J=8.4 Hz, 1H), 7.25 (d, J=1.8 Hz, 1H), 6.97 (dd, J=8.4, 1.8 Hz, 1H), 4.81 (t, J=5.4 Hz, 1H), 3.56 (q, J=5.7 Hz, 2H), 3.35 ppm (q, J=5.8 Hz, 2H).

Methanesulfonic acid 2-[(5-chloro-benzooxazol-2-yl)-(3-oxo-butyl)-amino]ethyl ester (3-4)

To a 1000 mL 3-neck round bottom flask equipped with a septum, thermocouple, inert gas inlet and magnetic stir bar was charged 3-3 (25.2 g, 119 mmol). To this flask was added 126 mL DMF, 12.2 mL methyl vinyl ketone (148 mmol) and 0.119 mL 10M NaOH (1.19 mmol). The reaction was then aged for 6 hours, at which time conversion was judged to be complete by HPLC. The solution was diluted with 252 mL iPAc and cooled to 0° C., then 23.1 mL Et$_3$N (166 mmol) followed by dropwise addition of 12.0 mL methanesulfonyl chloride (154 mmol) over 45 minutes, maintaining internal temperature less than 10° C. After a further 30 minutes, conversion was judged to be complete by HPLC. The solution was washed with 3×63 mL 5 w/w % aqueous NaHCO$_3$ solution, then 66 mL water. After cutting the aqueous layer, the organics were reduced to approximately two volumes or 50 mL iPAc. The organics were then agitated by an overhead stirrer during slow addition of 151 mL n-Heptane over 4 hours. Over this time a crystalline white precipitate developed, and was allowed to stir overnight. At this time there was a thick slurry, which was filtered and washed with 2×50 mL 90:10 n-Heptane:IPAc, and after drying with a nitrogen stream over the filter pad, 3-4 was obtained as a white crystalline solid (34.6 g., 96 mmol). $^1$H NMR (500 MHz, CDCl$_3$): δ=7.29 (s, 1H), 7.16 (d, J=8.2 Hz, 1H), 6.97 (d, J=7.8 Hz, 1H), 4.46 (s, 2H), 3.92 (s, 2H), 3.81 (t, J=5.9 Hz, 2H), 2.98-2.92 (m, 5H), 2.16 (s, 3H).

EXAMPLE 3

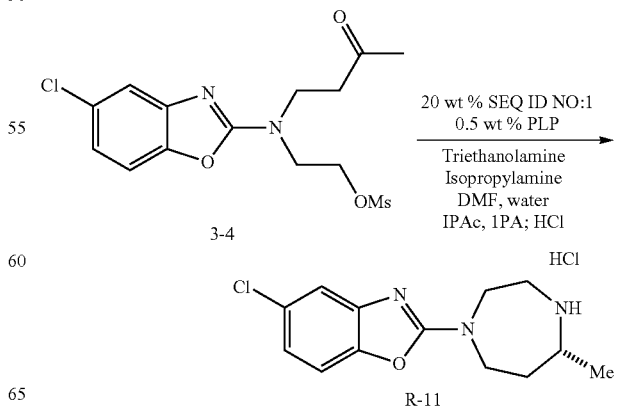

5-Chloro-2-((R)-5-methyl-[1,4]diazepan-1-yl)-benzooxazole hydrochloride (R-11)

To a 1000 mL 3-necked flask was charged isopropylamine hydrochloride (25.8 g., 270 mmol) and 525 mL 0.1 M aqueous triethanolamine solution. To this was added 750 mg pyridoxal 5'-phosphate hydrate (PLP) and 3.0 g of the transaminase polypeptide having the amino acid sequence SEQ ID NO:1 and the suspension was stirred until all components dissolved. The transaminase polypeptide having the amino acid sequence SEQ ID NO:1 was obtained as disclosed in US Patent Publication US 2010/0285541 for the identical sequence "SEQ ID NO:110" therein. The solution was heated to 40° C. and the pH of the solution was adjusted to pH 8.5 with an aqueous 4M solution of isopropylamine Mesylate 3-4 was added as a 225 mL DMSO solution via syringe over 6 hours, and the resulting mixture stirred for a further 5 hours. At this time, the solution was poured into a 3 L separatory funnel and extracted with 1.5 L of 1:1 iPAc:IPA. The aqueous layer was cut then extracted again with 750 mL 4:1 iPAc:IPA. The organics were combined, then washed with 750 mL brine. Then the organics were concentrated with IPA flushing to establish a 45 mL solution in IPA which was then treated with 4.6M HCl in IPA (9.94 mL, 45.7 mmol) via dropwise addition. The resulting solution was stirred vigorously while 52 mL IPAc was added slowly over 5 hours, creating a slurry of HCl salt 6. The slurry was then slowly cooled to 0° C. and allowed to stir overnight. At this time the slurry was filtered and dried with a nitrogen stream over the filter pad, providing R-11 as a white crystalline solid (7.80 g., 25.8 mmol). $^1$H NMR (500 MHz, CD$_3$OD): δ=7.13-7.10 (m, 2H), 6.97 (dd, J=8.2, 1.8 Hz, 1H), 3.99-3.79 (m, 3H), 3.67-3.57 (m, 3H), 3.39-3.33 (m, 1H), 2.24 (s, 1H), 2.12-2.07 (m, 1H), 1.42 (d, J=6.7 Hz, 3H).

EXAMPLE 4

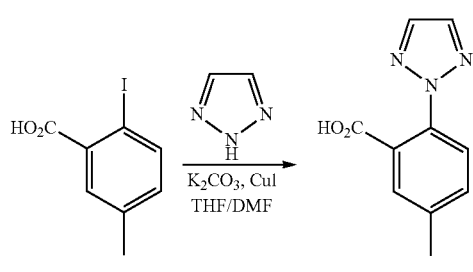

5-Methyl-2-[1,2,3]triazol-2-yl-benzoic acid (5)

The iodide 19 (6.04 kg, 23.0 mol), THF (45 L) and DMF (9.0 L) were charged to a vessel. Copper iodide (218 g, 1.15 mol) and potassium carbonate (7.94 kg, 57.4 mol) were added and the mixture heated to an internal temperature of 40° C. 1,2,3-Triazole (3.16 kg, 46.0 mol) was added as a solution in THF (6.0 L) over half an hour (no exotherm) and heating continued to 65° C. (again no exotherm observed) and the reaction monitored by HPLC. Once complete N,N-dimethylethylenediamine (244 mL, 2.30 mol) was added and mixture cooled to RT. Aqueous 3.6 M HCl (36 L) was added (exotherm) and the mixture extracted twice with ethyl acetate (2×30 L). The combined organics were washed with LiCl solution (2×20 L). The acid solution assayed for 3.79 kg of 5 (81%) and 4.64 kg of 5 and 20 combined (99%). A solution of acids 5 and 20 (approx. 4.64 kg, 22.9 mol) in THF and EtOAc (approx. 110 L) was concentrated to low volume. THF (90 L) was added and the solvent composition checked by $^1$H NMR to ensure most ethyl acetate had been removed. Sodium tert-butoxide (2.42 kg, 25.2 mol) was added slowly as a solid over 1-2 h (slight exotherm), allowing the sodium salt to form and stirred overnight at RT. The liquors showed a 45:55 ratio of product:starting material and the solid was collected by filtration, washed with THF (2×20 L) and dried in a vacuum oven (T=40° C.) for 15 h to afford 4.22 kg of crude sodium salt. The crude sodium salt (4.22 kg, 14.9 mol) was charged to a 50 L vessel and 3.6 M HCl (21.2 L) was added with cooling. The slurry was then stirred at room temperature for 16 h and the off-white solid isolated by filtration. The cake was washed with water (11 L) and iPAc/Heptane (2×5 L), then dried in a vacuum oven (T=35° C.) for 15 h to give 3.10 kg of crude acid 5 (97.9 LCAP, 92 wt %, corrected weight 2.85 kg, 61% yield from 19). The acid 5 (2.85 kg corrected, 14.0 mol) was charged to a 50 L vessel and EtOAc (28 L) and dilute 0.22 M HCl (14 L) were added and the mixture stirred until two clear phases resulted. The aqueous layer was removed and the organic layer filtered to remove any particulate matter. The ethyl acetate was reduced to about 8 L and then heptane (15.6 L) was added over 1 h and the liquors sampled to check for appropriate losses. The solid was isolated by filtration, washed with heptane:ethyl acetate (3:1, 4 L) and dried on the filter under nitrogen to give 2.81 kg of acid 5. m.p. 167.5° C. $^1$H NMR (400 MHz, d$_6$-DMSO): δ 12.09 (br s, 1H), 8.04 (s, 1H), 7.62 (d, 1H, J=8.4 Hz), 7.58 (d, 1H, J=1.2 Hz), 7.49 (dd, 1H, J=8.4, 1.2 Hz), 2.41 (s, 3H). $^{13}$C NMR (100.6 MHz, d$_6$-DMSO): δ 168.0, 139.2, 136.4, 135.8, 132.5, 130.3, 128.7, 124.8, 20.9. HRMS (ESI): m/z [M$^+$+H] calcd for C$_{10}$H$_9$N$_3$O$_2$: 204.0773; found: 204.0781.

EXAMPLE 5

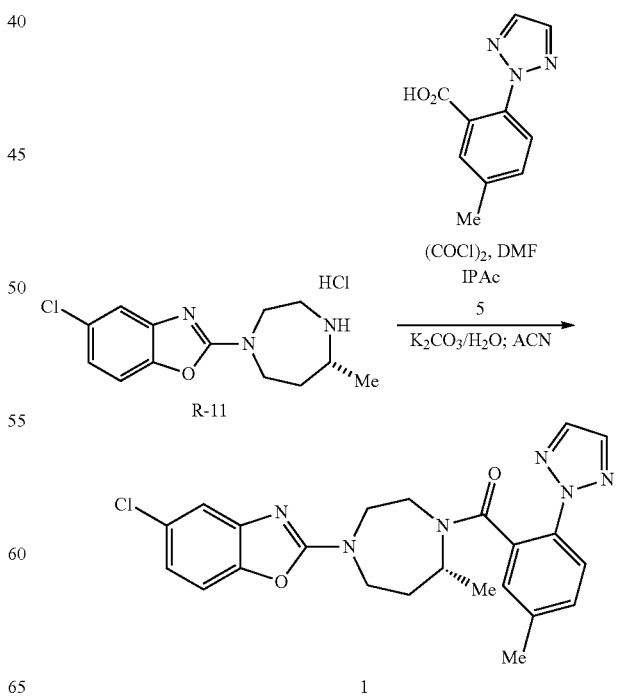

[(R)-4-(5-Chloro-benzooxazol-2-yl)-7-methyl-[1,4]diazepan-1-yl]-(5-methyl-2-[1,2,3]triazol-2-yl-phenyl)-methanone (1)

A round bottom flask was charged 6.86 g of 5-methyl-2-[1,2,3]triazol-2-yl-benzoic acid (5) along with 7.0 vol or 70 mls of dry iPAc (KF<200 ppm) forming a slurry. To this was charged 0.73 g of DMF then the system was purged thoroughly with nitrogen and temperature was set at 20° C.-25° C. 5.04 g of oxalyl chloride was added while maintaining 20° C.-25° C. and controlling off-gassing since it is extremely vigorous. With the feed of oxalyl chloride the previous slurry dissolved. The batch was aged for 1 hr, sampled for acid chloride formation (<1 LCAP) and allowed to proceed to amidation. In a separate vessel a solution of potassium carbonate was prepared in 5.0 vol or 50 mL water (note: exotherm). The solution was cooled to 0° C. When acid chloride (above) was prepared, added 2.5 vol or 25 mL iPAc to the aqueous solution with overhead stirring, then added 10.0 g amine hydrochloride salt (R-11) to solution, and stirred for 15 minutes. Then using a cannula, the acid chloride solution was transferred over from separate vessel over the course of 1 hour, maintaining less than 5° C. internal temperature. The vessel was flushed with 2.5 vol or 25 mL iPAc and sampled to determine completion. The slurry was heated to 40° C. Upon reaching 40° C., 1.5 vol or 15 mL Acetonitrile was and agitated for 5 minutes, and all material went into solution (98% AY observed). Agitation was stopped. After phase separation, the aqueous layer was cut, the organics were stirred with DARCO (10 wt % 6 basis) at 40° C. for 3 hours, then filtered hot and taken through to crystallization. Additional product was recovered from the carbon with an iPAc flush.

The batch was concentrated in iPAc and flushed to 7.5 vol (L/Kg of 1) and heated to 80-85 C until complete dissolution. The solution was cooled to 65° C. linearly over 2 hrs, and the agitation speed was adjusted to high. At 65° C., the solution was charged with 0.3 wt % seed in n-Heptane and aged for 1 hour. After the age and confirmation of the seed bed, the batch was cooled to 45° C. over 2.5 hrs. At this time a solvent switch was conducted at constant volume to a ratio of 90:10 n-Heptane:iPAc. The material was filtered hot at 45° C., the cake was washed with 3 vol (L/Kg of 1) of 90:10 n-Heptane:iPAc twice, followed by 3 vol (L/Kg of 1) of n-Heptane twice. The cake was dried at 70° C. under vacuum to give 14.4 g. 1 (31.8 mmol,) as a crystalline white powder.

EXAMPLE 6

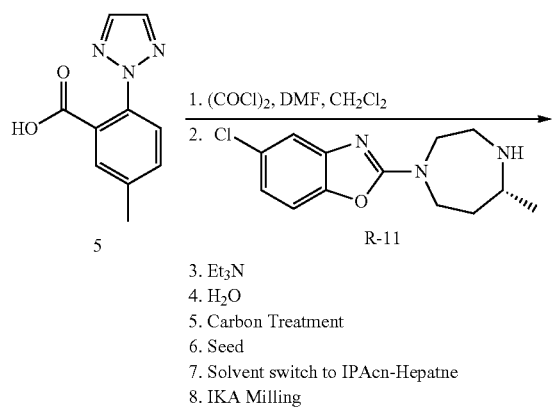

3. Et₃N
4. H₂O
5. Carbon Treatment
6. Seed
7. Solvent switch to IPAcn-Hepatne
8. IKA Milling

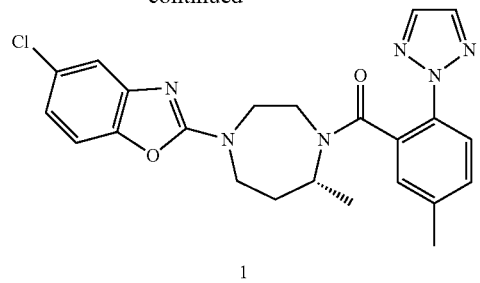

1

[(R)-4-(5-Chloro-benzooxazol-2-yl)-7-methyl-[1,4]diazepan-1-yl]-(5-methyl-2-[1,2,3]triazol-2-yl-phenyl)-methanone (1)

A reaction vessel was charged with 213.4 g of triazole acid (5) along with 7.4 vol or 2236 mls of dry iPAc (KF<200 ppm) forming a slurry. To this charge was added 21.93 g of DMF then the system was purged thoroughly with nitrogen and temperature was maintained at 20-25 C. Charged 152.3 g of oxalyl chloride while maintaining 20-25 C and control of off-gassing since it is extremely vigorous. With the feed of oxalyl chloride the previous slurry all dissolved. The batch was aged for 1 hr. The reaction was sampled for Acid Chloride formation (<1 LCAP) and proceeded to distillation. Distillation was conducted down to 1118 ml or constant volume distillation using 7.4 vol of fresh iPAc under vacuum maintaining less than 30° C.

In a separate vessel prepared a solution of 302.2 g of amine hydrochloride salt (R-11) in 15.3 vol or 4624 mls of dry iPAc (KF<200 ppm) to form a slurry. Then transferred the acid chloride solution using a cannula over from a separate vessel followed by flushing the vessel with 6.9 vol or 2085 mls of iPAc. With the amine and acid chloride in the same vessel began addition of 404.8 g of triethylamine. This charge was made over 1 to 4 hrs at a temperature between 20-40 C with a desired control of the temperature between 20-30 C. Once feed of the TEA was complete, the batch was aged for 1 hr and then sampled to determine completion.

Once the batch was complete, charged 7.4 vol of water or 2236 mls and then heated the solution to 40 C. Once at 40 C, the mixture was aged 5 minutes then agitation was stopped. The phases separated but there was an appreciable rag layer so it was allowed to settle and the rag was cut along with the aqueous layer. The aqueous rag was filtered then the aqueous layer was back extracted with 3.5 vol or 1058 ml of iPAc and all iPAc layers were combined.

The batch was recycled in iPAc (~60 g per kg of iPAc) via a Cuno filter (1 bundle per 39 Kg Amine HCl Salt) for several hours at 40° C. The batch was drummed off through a sparkler filter and additional material was recovered from the carbon with an iPAc flush.

The batch was concentrated in iPAc and flushed to 7.5 vol (L/Kg of product) and heated to 80-85° C. until complete dissolution. The mixture was cooled to 65° C. linearly over 2 hrs, and agitation speed was adjusted to high from this point forward. At 65° C., the mixture was charged with 0.3 wt % of [(R)-4-(5-chloro-benzooxazol-2-yl)-7-methyl-[1,4]diazepan-1-yl]-(5-methyl-2-[1,2,3]triazol-2-yl-phenyl)-methanone seed in n-Heptane and aged for 1-3 hour. After the age and confirmation of the seed bed, the batch was cooled to 45° C. over 2.5 hrs. A solvent switch was conducted at constant volume to a ratio of 90:10 n-Heptane:iPAc.

The batch was wet milled to a uniform particle size and filter hot at 45 C. The cake was washed with 3 vol (L/Kg of product) of 90:10 n-Heptane:iPAc twice, followed by 3 vol (L/Kg of product) of n-heptane twice. The cake was dried at 70° C. under vacuum.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A process for preparing a compound of the formula III:

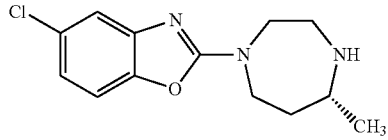

or a salt thereof,
which comprises:
contacting a compound of the formula IV:

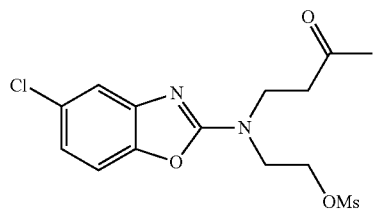

with a transaminase polypeptide, wherein the transaminase polypeptide is a transaminase polypeptide having the amino acid sequence of SEQ ID NO: 1 or the transaminase polypeptide of ATA-117, in the presence of a cofactor and in the presence of a weak base in a solvent, to give the compound of the formula III, or a salt thereof.

2. The process of claim 1 wherein the transaminase polypeptide is a transaminase polypeptide having the amino acid sequence of SEQ ID NO: 1.

3. The process of claim 1 wherein the transaminase polypeptide is ATA-117.

4. The process of claim 1 wherein the cofactor is a member of the vitamin B6 family.

5. The process of claim 1 wherein the cofactor is selected from the group consisting of pyridoxal (PL), pyridoxamine (PM), pyridoxine phosphate (PNP), pyridoxamine phosphate (PMP), and pyridoxal 5'-phosphate.

6. The process of claim 1 wherein the cofactor is pyridoxal 5'-phosphate.

7. The process of claim 1 wherein the weak base is selected from triethylamine, Hunig's base, triethanolamine, DBU, an inorganic carbonate, an inorganic bicarbonate, an inorganic phosphate, and an inorganic hydroxide.

8. The process of claim 7 wherein the weak base is triethylamine.

9. The process of claim 1 wherein the solvent for the process comprises a solvent that is selected from 1-methyl-2-pyrroldinone, 1-ethyl-2-pyrroldinone, DMSO, DMF, DMA, MeOH, acetonitrile and water.

10. The process of claim 9 wherein the solvent for the process comprises DMF.

11. The process of claim 1 wherein the process is conducted at a temperature between about 20 and 60° C.

* * * * *